United States Patent [19]
Imazato et al.

[11] Patent Number: 5,733,949
[45] Date of Patent: Mar. 31, 1998

[54] ANTIMICROBIAL ADHESIVE COMPOSITION FOR DENTAL USES

[75] Inventors: Satoshi Imazato; Mitsuo Torii, both of Suita; Yasuhiko Tsuchitani, Nara; Hideaki Yamada; Nobuyuki Utagawa, both of Kurashiki, all of Japan

[73] Assignee: Kuraray Co., Ltd., Kurashiki, Japan

[21] Appl. No.: 539,833

[22] Filed: Oct. 6, 1995

[30] Foreign Application Priority Data

Oct. 7, 1994 [JP] Japan ................. 6-243781

[51] Int. Cl.$^6$ ................. A61K 6/10; C08L 39/00
[52] U.S. Cl. ................. 523/109; 524/800; 524/808; 526/89
[58] Field of Search ................. 523/109; 524/800, 524/808; 526/89

[56] References Cited

U.S. PATENT DOCUMENTS

| | | | |
|---|---|---|---|
| 4,871,786 | 10/1989 | Aasen et al. | 523/113 |
| 5,196,135 | 3/1993 | Merianos | 252/106 |
| 5,264,513 | 11/1993 | Ikemura et al. | 526/318 |
| 5,408,022 | 4/1995 | Imazato et al. | 526/259 |
| 5,494,987 | 2/1996 | Imazato et al. | 526/263 |

FOREIGN PATENT DOCUMENTS

| | | |
|---|---|---|
| 115410 | 8/1984 | European Pat. Off. . |
| 526654 | 2/1993 | European Pat. Off. . |
| 537774 | 4/1993 | European Pat. Off. . |
| 602254 | 6/1994 | European Pat. Off. . |

*Primary Examiner*—Kriellion S. Morgan
*Attorney, Agent, or Firm*—Oblon, Spivak, McClelland, Maier & Neustadt, P.C.

[57] ABSTRACT

An antimicrobial adhesive composition for dental use comprising the following polymerizable monomers: an antimicrobial monomer, an monomer containing at least one acidic group, and a monomer containing at least one alcoholic hydroxy group, in combination with water and a polymerization catalyst.

14 Claims, No Drawings

ANTIMICROBIAL ADHESIVE COMPOSITION FOR DENTAL USES

BACKGROUND OF THE INVENTION

1. Field of the Invention

The present invention relates to an antimicrobial adhesive composition for dental use.

2. Description of the Prior Art

In prosthodontic treatment using restorative materials such as composite resins, dental alloys and ceramics, acrylic adhesives are often used. However, such restorative materials generally show insufficient adhesion to the teeth surface such that they may fall off from the surface or there may occur secondary caries or pulpitis due to invasion of bacteria at the interface between the tooth and the restorative material.

In order to solve these and other problems, it has been proposed to give pretreatment to the tooth surface using various types of surface treatment agents. It is reported that adhesion between the tooth surface and the restorative material improves by such pretreatment: (1) an article appearing in Journal of Dental Research (Vol. 34, pp 849–853, 1955) states that so-called acid etching technique improves adhesion between the restorative material and the enamel: (2) an article in Journal of Dental Research (Vol. 63, pp 1087–1089, 1984) describes that a primer composition comprising glutaraldehyde, 2-hydroxyethylmethacrylate (hereinafter HEMA) and water reinforces adhesion between the restorative material and the enamel; (3) Japanese Patent Application (JPA) Kokai No. Sho62-223289 discloses that a primer obtained by adding to aqueous HEMA solution acids such as maleic acid, tribromoacetate or chloric acid significantly improves adhesion between the restorative material and the enamel or dentin; (4) an article in SHIKA ZAIRYO KIKAI (Vol. 9 pp 65–73, 1990) reports that a primer comprising an aqueous HEMA solution added with a monomer containing amino acid residues such as N-methacryloylalanine and N-acryloylalanine greatly improves the adhesion in question; (5) JPA Kokai No. Hei 3-240712 discloses a primer composition comprising (i) 0.5–90% by weight of water, (ii) 5–90% by weight of a polymerizable composition having alcoholic hydroxy group, (iii) 0.1–90% by weight of a polymerizable composition having acidic group, and (iv) 0.01–30% by weight of amino compounds having acidic group; and (6) JPA Kokai No. Hei 4-8368 describes that a radical improvement in adhesive strength between the restorative material and the dentin is achieved when an amino compound is added to the above mentioned composition.

Although such pretreatment improves adhesive strength between the tooth surface and the restorative material, there still remains the problem of secondary caries or pulpitis occurring due to microbial invasion from the adhesion interface.

Attempts have also been made to impart antimicrobial property to dental adhesives. For example, JPA Kokai No. Hei 1-17107 discloses dental cement containing an antimicrobial agent, and JPA Kokai Hei 6-9725 describes a dental composition which contains an antimicrobial polymerizable monomer and a polymerizable monomer having acidic group. However, the former dental cement containing an antimicrobial agent does have problems in that said antimicrobial agent becomes eluted in the oral cavity and destroys the oral bacterial flora and that resistant microorganisms may appear, requiring thorough safety study prior to clinical application. As for the latter dental composition containing an antimicrobial polymerizable monomer, it is capable of reducing bacteria adhered on the surface of polymerized substance because the antimicrobial agent is non-releasable on the cured surface. However, it is not capable of killing the microorganisms remaining in the microstructure such as dentinal tubules at the adhesion interface.

SUMMARY OF THE INVENTION

The present invention has been made in view of the problems encountered in the prior art, and aims at providing an antimicrobial composition for dental use capable of improving adhesive strength between the tooth and the restorative material to thereby prevent microbial invasion at the interface and kill microorganisms remaining in the microstructure such as dentinal tubules or invading at the interface after adhesion.

The present inventors found that further blending of a polymerizable monomer having alcoholic hydroxy group and water to said dental composition containing an antimicrobial polymerizable monomer and a polymerizable monomer having acidic group is effective in promoting penetration of the antimicrobial agent into the microstructure at the adhesion interface such as dentinal tubules, and killing the microorganisms remaining in such microstructure and those invading the microstructure after the composition has been polymerized and cured.

The object of the present invention is therefore to provide an antimicrobial dental composition comprising (A) 0.01–25 wt % of antimicrobial polymerizable monomer, (B) 5–40 wt % of polymerizable monomer having acidic group, (C) 10–50 wt % of polymerizable monomer having alcoholic hydroxy group, (D) 20–75 wt % of water, and a polymerization catalyst.

DETAILED DESCRIPTION OF THE INVENTION

In the antimicrobial dental composition according to the present invention, it is essential to combine antimicrobial polymerizable monomer (A), polymerizable monomer having acidic group (B), polymerizable monomer having alcoholic hydroxy group (C), and water (D). If antimicrobial polymerizable monomer (A) alone is used, the antimicrobial action would be insufficient and would be merely effective in reducing microorganisms adhered to the cured surface, as is indicated in the data hereinbelow. Combining a polymerizable monomer having acidic group (B), a polymerizable monomer having alcoholic hydroxy group (C) and water in accordance with the present invention promotes penetration of the antimicrobial component into the microstructure at the interface such as dentinal tubules and enables killing of the microorganisms remaining therein during the primer treatment. As the non-elute type antimicrobial property develops on the cured surface of the composition after polymerization has taken place, microorganisms that invade from the adhesion interface between the tooth and the restorative material can also be killed. The present invention provides a composition having such a function for the first time in the art. It is noted that the term "adhesive" used in this invention means both a primer which is directly applied on the tooth before another adhesive is applied and an adhesive which is used to bond the tooth and the dental restorative material without using another adhesive.

In order for the antimicrobial property to be fully exhibited during the primer treatment, it is essential to use said antimicrobial polymerizable monomer (A), polymerizable monomer having alcoholic hydroxy group (C) and water.

The antimicrobial property obtained would be insufficient if any one of these components is absent.

In order to secure non-elute type antimicrobial property fully after polymerization and curing of the composition, it is essential to combine antimicrobial polymerizable monomer (A) and polymerizable monomer with acidic group (B). If only one of the two components is used, the antimicrobial property will be diminished and the microorganisms invading at the interface cannot be destroyed.

In order for the composition to fully exhibit its original function as a dental primer of improving the adhesive strength between the tooth and the restorative material, it is necessary to use polymerizable monomer having acidic group (B) and polymerizable monomer having alcoholic hydroxy group (C) and water in combination.

Thus, the combined use of antimicrobial polymerizable monomer (A), polymerizable monomer with acidic group (B) and polymerizable monomer with alcoholic hydroxy group (C) is essential in order to meet the three requirements for the composition of exhibiting antimicrobial property during the primer application, non-elute type antimicrobial property after polymerization and curing, and improved adhesive strength between the tooth and the restorative material.

Preferred antimicrobial polymerizable monomer (A) includes monomers having the chemical structures shown below as Chemical Formula 1, Chemical Formula 2 and Chemical Formula 3.

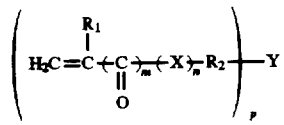

Chemical Formula 1

$R_1$=H, $CH_3$ $R_2$=Alkylene group of $C_8$–$C_{25}$

X=O,S,

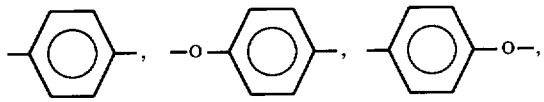

—$CH_2O$—, —$OCH_2$— m=0 or 1 n=0 or 1 p=1–3

Y=

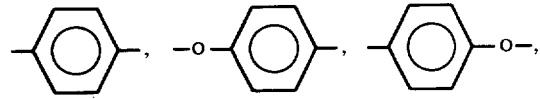

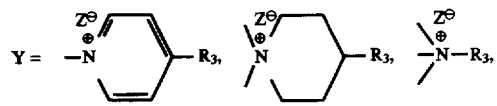

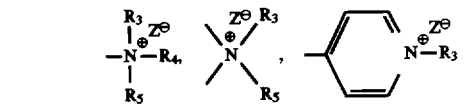

$R_3$, $R_4$, $R_5$=–(X–)$_q$–$R_6$-W

X=O,S,

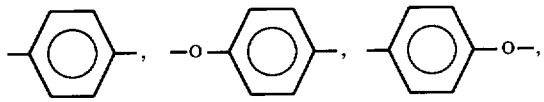

—$CH_2O$—, —$OCH_2$—

$R_6$=Alkylene group of $C_8$–$C_{25}$

W=—H, —$CH_3$,

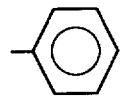

q=0 or 1

Z=Cl, Br, I

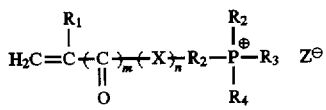

Chemical Formula 2

$R_1$=$CH_3$, H

X=O,S,

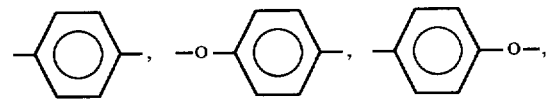

—$CH_2O$—, —$OCH_2$— m=0 or 1 n=0 or 1

$R_2$, $R_3$, $R_4$=–(X–)$_q$–$R_5$-W $R_5$=Alkylene group of $C_8$–$C_{25}$

W=—H, $CH_3$,

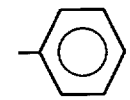

q=0 or 1

Z=Cl, Br, I

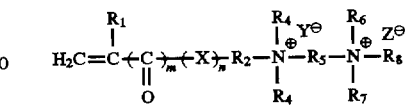

Chemical Formula 3

$R_1$=H, $CH_3$ $R_2$=Alkylene group of $C_8$–$C_{25}$

X=O,S,

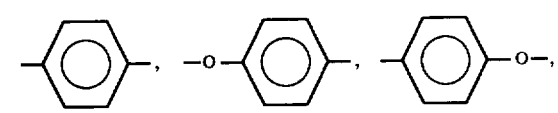

—$CH_2O$—, —$OCH_2$— m=0 or 1 n=0 or 1

$R_3$, $R_4$, $R_6$, $R_7$=H or $C_1$–$C_{20}$ alkyl $R_5$=Alkylene group of $C_1$–$C_{20}$ $R_8$=H, or $C_1$–$C_{20}$ alkyl, or

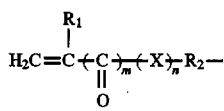

Z, Y=Cl, Br, I

The amount of antimicrobial polymerizable monomer (A) to be used in the present invention must be within the range of 0.01 to 25 wt % of the composition as a whole, and more preferably between 0.1 and 20 wt. %. If it is less than 0.01 wt. %, the antimicrobial property will be insufficient and microorganisms remaining in or invading at the adhesion interface between the tooth and the restorative material cannot be destroyed. On the other hand, if said amount exceeds 25 wt % as against the entire composition, the adhesive strength between the tooth and the restorative material cannot be improved.

Polymerizable monomer having acidic group (B) used in the present invention may be polymerizable monomers having acidic group such as phosphoric acid group, carboxylic acid group, sulfonic acid group and acid anhydride residues, and polymerizable unsaturated group such as acryloyl group, methacryloyl group and vinyl group. They include, for example, compounds containing phosphoric acid monoester group such as 2-(meth)acryloyloxyethyl dihydrogen phosphate, 6-(meth)acryloyloxyhexyl dihydrogen phosphate, 10-(meth)acryloyloxydecyl dihydrogen phosphate, and 2-(meth)acryloyloxyethylphenyl dihydrogen phosphate; compounds containing phosphoric acid diesters such as bis(2-(meth)acryloyloxyethyl) hydrogen phosphate, 2-(meth)acryloyloxyethyl hydrogen phenylphosphate, and 2-(meth)acryloyloxyethyl hydrogen anicylphosphate; derivatives of phosphoric acid such as 6-(meth)acryloyloxyhexyl phosphinate, N-(10-phosphonodecyl)-(meth)acrylamide, 4-vinylbenzene-phosphate, and 4-vinylbenzyl phosphate; compounds containing carboxylic group such as (meth)acrylic acid, succinic acid mono(2-(meth)-acryloxyloxyethyl), isophthalic acid (2-(meth) acryloyloxyethyl), 4-(meth)acryloyloxyethyl trimellitic acid, 11,11-dicarboxyundecyl(meth)acrylate, N-(meth) acryloylalamine, N-(meth)acryloyl-5-aminosalicylic acid, 4-vinylbenzoic acid, and anhydrides thereof; and compounds containing sulfonic acid group such as 2-(meth) acrylamide-2-methylpropane sulfonic acid and styrene sulfonic acid.

The amount of polymerizable monomer having acidic group (B) used in the present invention should be within the base range of from 5 to 40 wt % based on the total weight of the composition, and more preferably between 10 to 30 wt %. If said amount is less than 5 wt % of the composition, the antimicrobial property obtained would be insufficient, failing to destroy the microorganisms remaining in or invading at the adhesion interface of the tooth and the restorative material. If said amount exceeds 40 wt % of the composition, the adhesive strength between the tooth and the restorative material would not be improved. Two or more kinds of polymerizable monomer having acidic group may be used in combination.

Polymerizable monomer having alcoholic hydroxy group (C) may be polymerizable monomers having alcoholic hydroxy group and polymerizable unsaturated group such as alcoholic hydroxy group, acryloyl group, methacryloyl group and vinyl group. They may include 2-hydroxyethyl (meth)acrylate, propylene-glycolmono(meth)acrylate, glycerinemono(meth)acrylate, erythritolmono(meth) acrylate, penthaerythritol-di(meth)acrylate, 1,2-bis(3-methacroyloyloxy-2-hydroxypropoxy)ethane, N-methylol (meth)acrylamide, N-hydroxyethyl(meth)acrylamide, and N,N(dihydroxyethyl)(meth)acrylamide.

The content of polymerizable monomer having alcoholic hydroxy group (C) must be in the range of from 10 to 50 wt % of the composition, and more preferably between 15 and 40 wt %. If it is less than 10 wt % or exceeds 50 wt %, the adhesive strength between the tooth and the restorative material cannot be improved. Two or more kinds of polymerizable monomer having alcoholic hydroxy group (C) many be used in combination.

Water used in the present invention must not contain substantial amounts of any impurities which adversely affect the adhesive strength between the tooth and the restorative material or the antimicrobial property, and is preferably distilled or ion-exchanged water. The water content must fall within the range of from 20 to 75 wt % of the composition, and preferably between 25 and 60 wt %. If it is less than 20 wt % or exceeds 75 wt %, then the adhesive strength between the tooth and the restorative material cannot be improved.

If desired, a water miscible solvent such as ethanol and acetone may be added.

Examples of polymerization catalyst to be used in the present invention may include organic peroxides such as benzoyl peroxide and cumenhydroperoxides; initiators for cold polymerization such as tributylborane, benzoyl peroxides/aromatic tertiary amines, aromatic sulfinic acid (or salt thereof)/aromatic secondary or tertiary amine/ acrylperoxides; initiators for photopolymerization such as camphorquinone, camphorquinone/p-dimethylaminobenzoic acid esters, camphorquinone/p-dimethylaminobenzophenone, camphorquinone/ aromaticsulfinic acid salt, camphorquinone/peroxides, camphorquinone/aldehydes, camphorquinone/mercaptans, and acylphosphin oxides. For photopolymerization under ultraviolet irradiation, it is preferable to use benzoinmethylether, benzyldimethylketal, benzophenone, 2-ethylthioxanthone, diacetyl, benzyl, azobisisobutylonitril, and tetramethylthiuram disulfide. It is also possible to use initiators for cold polymerization and for photopolymerization simultaneously. The polymerization catalyst is used within the range of from 2 to 15 wt % of the composition.

The antimicrobial adhesive composition for dental use according to the present invention may, if desired, contain added polymerizable monomers of acrylic base having no alcoholic hydroxy or acidic group. Polymerization inhibitors, coloring agents and ultraviolet light absorbing agents may also be added.

Examples of said polymerizable monomers of acrylic base without alcoholic hydroxy or acidic group include methyl(meth)acrylate, butyl(meth)acrylate, 2-(dimethylamino)ethyl(meth)acrylate, γ-methacryloyloxypropyltrimethoxysilane, triethyleneglycoldi(meth)acrylate, neopenthylglycol-di (meth)acrylate, 1,6-hexanediol-di(meth)acrylate, 1,10-decandioldi(meth)acrylate, 2,2'-bis[(meth) acryloyloxypolyethoxy)phenyl]propane, 2,2'-bis[4-(3-(meth)acryloyloxy-2-hydroxypropoxy)phenyl]propane, and trimethylolpropane-tri(meth)acrylate.

The antimicrobial adhesive composition for dental uses according to the present invention is applied on the tooth surface in accordance with the routine method of dentistry and requires no cleaning with water; and it is polymerized and cured at the adhesion interface between the tooth and the restorative material. The composition may be cured alone or partly mixed with dental adhesive.

Examples of said dental adhesives usually include acrylic adhesives such as those comprising polymerizable monomer of acrylic base and polymerization initiator. If necessary a filler may also be added to the composition. Acrylic adhesives comprising polymerizable monomer of acrylic base such as methyl(meth)acrylate, butyl(meth)acrylate, 2-hydroxyethyl(meth)acrylate, 2-(dimethylamino)ethyl (meth)acrylate, γ-methacryloyloxypropyltrimethoxysilane, triethyleneglycoldi(meth)acrylate, neopentylglycoldi(meth)acrylate, 2,2'bis[(meth)acryloyloxypolyethoxy)phenyl] propane, 2,2'-bis[4-(3(meth)acryloyloxy-2-hydroxypropoxy)phenyl]propane, 10-(meth)acryloyloxydecyl dihydrogen phosphate, 2-(meth)acrylolyloxyhylphenyl hydrogen phosphate, bis[2-(meth)acryloyloxyethyl]hydrogenphosphate, 4-(meth)acryloyloxyethyl trimellitic acid, 4-(meth)acryloyloxyethyl trimellitic acid anhydrides may be added; polymerization initiators such as benzoyl peroxide, benzoylperoxide/aromatic tertiary amines, aromatic sulfinic acid (or salts thereof), aromatic secondary or tertiary amines/acylperoxides, camphorquinones, camphorquinone/tertiary amines, camphorquinone/peroxides, and acyl phosphin oxides may be added; and fillers such as α-quartz, silica, alumina, hydroxyapatite, fluoroaluminosilicate glass, barium sulfate, titanium oxide, zirconia, silica glass, soda-lime silicate glass, barium glass as well as organic composite fillers containing organic and inorganic components may be added.

The present invention will now be described by way of examples, but it is in no way intended to be limited by these examples. The adhesive strength and the antimicrobial property were evaluated by the methods described below.

Test Method for Adhesive Strength

Bovine anterior tooth was subjected to wet polishing using No. 1000 silicon carbide polishing paper (manufactured by Nippon Kenshi Co., Ltd.) to expose the enamel or dentin surface, and the moisture on the surface was blown away with a dental air syringe. A tape having a bore measuring 5 mm in diameter was pasted on the exposed enamel or dentin surface, and the present invention adhesive composition was applied in the bore using a brush. The tooth was left standing for 30 seconds before drying with the air syringe. Commercial dental bonding agent "Clearfil LB Bond" (manufactured by Kuraray Co. Ltd.) was applied in a thickness of about 100 μm over the coating using a brush and irradiated with light for 20 seconds using a dental light projector "Litel II" (manufactured by Gumma Ushio Denki Co. Ltd.) for curing. A commercial photopolymerizable dental composite resin "Photoclearfil A" (manufactured by Kuraray Co. Ltd.) was placed over the coating, covered with a film comprising Eval® (manufactured by Kuraray Co. Ltd.), pressed down with a slide glass from above, and then irradiated with light using said light projector for 40 seconds for curing. A stainless rod was adhered to the cured surface using a commercial dental resin cement "Panavia 21" (manufactured by Kuraray Co. Ltd.), left standing for 15 minutes, and immersed in water at 37° C. Tensile strength of the adhesive was measured after 24 hours.

Test Method 1 for Antimicrobial Activity—
Evaluation of Antimicrobial Activity during Primer Treatment Bovine anterior tooth was polished with a No. 1000 silicon carbide polishing paper (manufactured by Nippon Kenshi Co. Ltd.) in wet condition to expose the dentin surface and then cut into 1 mm thick specimens using a diamond saw. The specimen was applied with a 40% aqueous solution of phosphoric acid on both surfaces, left standing for 60 seconds, cleansed with running water and kept submerged in water for storage until use.

Streptococcus mutans IFO 13955 which had been cultured in advance for 24 hours in a BHI broth (brain heart infusion) (manufactured by Nissui Seiyaku K.K.) was diluted with sterilized physiological saline to a bacterial content of $1\times10^4$ (CFU/ml), inoculated on the BHI agar medium for an amount of 100 μl, and spread evenly over the entire surface using a conradi.

The dentin specimen mentioned above was pasted with a tape having a hole of 5 mm diameter, and pressed lightly onto the center of the agar medium. The adhesive composition according to the present invention was applied using a brush to the hole of the specimen placed on the medium and was left standing for 60 seconds to allow the composition to penetrate into the specimen tissues. The specimen was then removed from the medium, and the BHI medium was cultured at 37° C. for 48 hours. Microbial proliferation was observed and the result was evaluated based on the following criteria.

++) Microbial proliferation is observed even in the region where the specimen was placed. (The antimicrobial component is not recognized to have penetrated into the specimen tissues.)

+) Microbial proliferation is restricted in the specimen region when compared with the surrounding region. (The antimicrobial component is recognized to have penetrated into the specimen tissues to a limited extent).

−) No microbial proliferation is observed in the specimen region. (The antimicrobial component has fully penetrated into the specimen tissues.)

Test Method 2 for Antimicrobial Activity—
Evaluation of Antimicrobial Activity on the Polymerized/Cured Surface A film made of Eval® was pasted with a tape having a hole with an inner diameter of 9 mm. A doughnut shaped mold (15 mm inner diameter, 40 mm outer diameter, 0.5 mm thickness) was placed over the film to maintain the same horizontal. The present invention adhesive composition was dropped into the die hole for an amount of 10 μl and dried using a dental air syringe. Clearfil LB Bond was applied over the film in a thickness of about 100 μm using a brush, and irradiated with light using a dental light projector "Litel II" for 20 seconds for curing. Photoclearfil A was placed over the coating, covered with Eval® film, pressed with a slide glass from above, and then irradiated with light for 40 seconds using said light projector for curing. The cured substance was removed from the die and cleansed ultrasonically in water for one hour.

Streptococcus mutans IFO 13955 which had been cultured in advance for 24 hours in BHI broth (manufactured by Nigsui Seiyaku K.K.) was diluted with sterilized physiological saline to a bacterial content of $1\times10^4$ (CFU/ml), and inoculated on said cured surface for an amount of 100 μl. The substance was left standing for 15 minutes, turned up side down and placed on the BHI agar medium to recover the bacterial solution. The cured substance was then pressed against another portion of the agar medium to completely remove the residual microorganisms adhered to the cured surface to be used as the sample. At the same time, 100 μl of the diluted microbial solution was directly inoculated on a BHI agar medium to be used as a control. These samples were cultured anaerobically at 37° C. for 24 hours, and aerobically for another 24 hours, and colonies formed were counted. The microbial death ratio was calculated by the following equation:

Death ratio of microorganisms =

$$\frac{\text{Number of colonies (control)} - \text{Number of colonies (sample)}}{\text{Number of colonies (control)}} \times 100$$

EXAMPLES 1–4

Adhesive compositions were prepared by blending 12-methacryloyloxydodecylpyridiniumbromide (hereinafter MDPB, the chemical structure shown below as Chemical Formula 4) as an antimicrobial polymerizable monomer, β-methacryloyloxyethylphenylphosphate (hereinafter phenyl P, the chemical structure shown below as Chemical Formula 5) as an antimicrobial polymerizable monomer, HEMA, distilled water, N,N-diethanol-p-toluidine (hereinafter DEPT), camphorquinone (hereinafter CQ), N,N-dimethylaminobenzoic acid isoamyl (hereinafter IADMAB), and ethanol in varying weight ratios as shown in Table 1. The adhesive strength measurements and antimicrobial activity tests 1 and 2 were conducted in the manner mentioned above. The results are shown in Table 1.

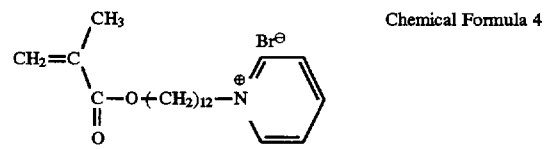

Chemical Formula 4

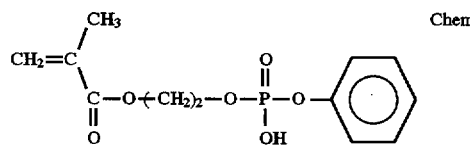

Chemical Formula 5

EXAMPLE 5–8

Adhesive compositions were prepared by blending MDPB, 10-methacryloyloxydecyl dihydrogen phosphate (hereinafter MDP, the chemical structure shown below as Chemical Formula 6), HEMA, distilled water, benzene sodium sulfinate (hereinafter abbreviated as BSS), and DEPT in varying weight ratios as shown in Table 3. The adhesive strength measurements and antimicrobial activity tests 1 and 2 were conducted in the manner mentioned above. The results are shown in Table 3.

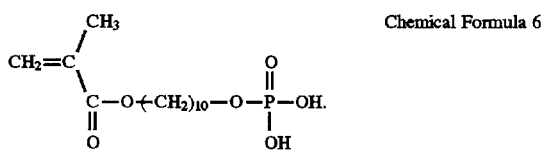

Chemical Formula 6

EXAMPLES 9–12

Adhesive compositions were prepared by blending MDPB, MDP, HBMA, distilled water, DEPT, CQ, IADMAB and ethanol in varying weight ratios shown in Table 1. The adhesive strength measurements and antimicrobial activity tests 1 and 2 were conducted in the manner mentioned above. The results are shown in Table 1.

EXAMPLES 13–16

Adhesive compositions were prepared by blending MDPB, methacrylic acid, HEMA, distilled water, DEPT, CQ, IADMAB, and ethanol in varying weight ratios shown in Table 1. The adhesive strength measurements and antimicrobial activity tests 1 and 2 were conducted in the manner mentioned above. The results are shown in Table 1.

EXAMPLES 17–20

Adhesive compositions were prepared by blending MDPB, 4-methacryloyloxyethyl trimellitic acid (hereinafter 4-MET), HEMA, distilled water, DEPT, CQ, IADMAB and ethanol in varying weight ratios shown in Table 2. The adhesive strength measurements and antimicrobial activity tests 1 and 2 were conducted in the manner mentioned above. The results are shown in Table 2.

EXAMPLES 21–24

Adhesive compositions were prepared by blending MDPB, 4-methacryloyloxyethyl trimellitic acid anhydride (hereinafter 4-META), HEMA, distilled water, DEPT, CQ, IADMAB and ethanol in varying weight ratios shown in Table 2. The adhesive conducted in the manner described above. The results are shown in Table 3.

EXAMPLES 37–40

Adhesive compositions were prepared by blending an antimicrobial polymerizable monomer having the chemical structure shown below as Chemical Formula 7 (hereinafter D-301 monomer), phenyl P, HEMA, distilled water, BSS and DEPT in varying weight ratios shown in Table 4. The adhesive strength measurements and antimicrobial activity tests 1 and 2 were conducted in the manner described above. The results are shown in Table 4.

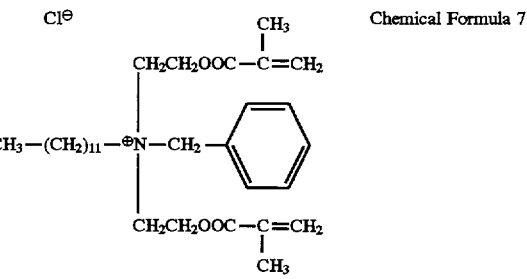

Chemical Formula 7

EXAMPLES 41–44

Adhesive compositions were prepared by blending D-301 monomer, MDP, HEMA, distilled water, BSS and DEPT in varying weight ratios shown in Table 4. The adhesive strength measurements and antimicrobial activity tests 1 and 2 were strength measurements and antimicrobial activity tests 1 and 2 were in the manner mentioned above. The results are shown in Table 2.

EXAMPLES 25–28

Adhesive compositions were prepared by blending MDPB, 4-acryloyloxyethyl trimellitic acid (hereinafter 4-AET), HEMA, distilled water, DEPT, CQ, IADMAB and ethanol in varying weight ratios shown in Table 2. The adhesive strength measurements and antimicrobial activity tests 1 and 2 were conducted in the manner mentioned above. The results are shown in Table 2.

EXAMPLES 29–32

Adhesive compositions were prepared by blending MDPB, phenyl P, HEMA, distilled water, BSS and DEPT in varying weight ratios shown in Table 3. The adhesive strength measurements and antimicrobial activity tests 1 and 2 were conducted in the manner described above. The results are shown in Table 3.

EXAMPLES 33–36

Adhesive compositions were prepared by blending MDPB, methacrylic acid, HEMA, distilled water, BSS and DEPT in varying weight ratios shown in Table 3. The adhesive strength measurements and antimicrobial activity tests 1 and 2 were conducted in the manner described above. The results are shown in Table 4.

EXAMPLES 45–48

Adhesive compositions were prepared by blending an antimicrobial polymerizable monomer having the chemical structure shown below as Chemical Formula 8 (hereinafter abbreviated as VB-16 monomer), phenyl P, HEMA, distilled water, BSS and DEPT in varying weight ratios shown in Table 4. The adhesive strength measurements and antimicrobial activity tests 1 and 2 were conducted in the manner described above. The results are shown in Table 4.

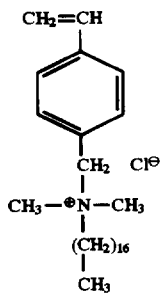

Chemical Formula 8

COMPARATIVE EXAMPLES 1 AND 2

Adhesive compositions were prepared by blending MDPB, phenyl P, HEMA, distilled water, DEPT, CQ, IADMAB, and ethanol in the weight ratios shown in Table 5. The adhesive strength measurements and antimicrobial activity tests 1 and 2 were conducted in the manner described above. The results are shown in Table 5.

COMPARATIVE EXAMPLES 3 AND 4

Adhesive compositions were prepared by blending MDPB, MDP, HEMA, distilled water, BSS and DEPT in the weight ratios shown in Table 7. The adhesive strength measurements and antimicrobial activity tests 1 and 2 were conducted in the manner described above. The results are shown in Table 7.

COMPARATIVE EXAMPLES 5 AND 6

Adhesive compositions were prepared by blending MDPB, HEMA, distilled water, DEPT, CQ, IADMAB and ethanol in the weight ratios shown in Table 5. The adhesive strength measurements and antimicrobial activity tests 1 and 2 were conducted in the manner described above. The results are shown in Table 5.

COMPARATIVE EXAMPLES 7–10

Adhesive compositions were prepared by blending MDPB, phenyl P, HEMA, DEPT, CQ, IADMAB and ethanol in the weight ratios shown in Table 5. The adhesive strength measurements and antimicrobial activity tests 1 and 2 were conducted in the manner described above. The results are shown in Table 5.

COMPARATIVE EXAMPLES 11–14

Adhesive compositions were prepared by blending MDPB, phenyl P, distilled water, DEPT, CQ, IADMAB and ethanol in the weight ratios shown in Table 5. The adhesive strength measurements and antimicrobial activity tests 1 and 2 were conducted in the manner described above. The results are shown in Table 5.

COMPARATIVE EXAMPLES 15 AND 16

Adhesive compositions were prepared by blending MDPB, MDP, HEMA, distilled water, DEPT, CQ, IADMAB and ethanol in the weight ratios shown in Table 6. The adhesive strength measurements and antimicrobial activity tests 1 and 2 were conducted in the manner described above. The results are shown in Table 6.

COMPARATIVE EXAMPLES 17 AND 18

Adhesive compositions were prepared by blending MDPB, HEMA, distilled water, DEPT, CQ, IADMAB and ethanol in the weight ratios shown in Table 6. The adhesive strength measurements and antimicrobial activity tests 1 and 2 were conducted in the manner described above. The results are shown in Table 6.

COMPARATIVE EXAMPLES 19–22

Adhesive compositions were prepared by blending MDPB, MDP, HEMA, DEPT, CQ, IADMAB and ethanol in the weight ratios shown in Table 6. The adhesive strength measurements and antimicrobial activity tests 1 and 2 were conducted in the manner described above. The results are shown in Table 6.

COMPARATIVE EXAMPLES 23–26

Adhesive compositions were prepared by blending MDPB, MDP, distilled water, DEPT, CQ, IADMAB and ethanol in the weight ratios shown in Table 6. The adhesive strength measurements and antimicrobial activity tests 1 and 2 were conducted in the manner described above. The results are shown in Table 6.

COMPARATIVE EXAMPLES 27 AND 28

Adhesive compositions were prepared by blending MDPB, HEMA, distilled water, BSS and DEPT in the weight ratios shown in Table 7. The adhesive strength measurements and antimicrobial activity tests 1 and 2 were conducted in the manner described above. The results are shown in Table 7.

COMPARATIVE EXAMPLES 29–32

Adhesive compositions were prepared by blending MDPB, MDP, HEMA, BSS and DEPT in the weight ratios shown in Table 7. The adhesive strength measurements and antimicrobial activity tests 1 and 2 were conducted in the manner described above. The results are shown in Table 7.

COMPARATIVE EXAMPLES 33–36

Adhesive compositions were prepared by blending MDPB, MDP, distilled water, BSS and DEPT in the weight ratios shown in Table 7. The adhesive strength measurements and antimicrobial activity tests 1 and 2 were conducted in the manner described above. The results are shown in Table 7.

COMPARATIVE EXAMPLES 37–41

Adhesive compositions were prepared by blending MDPB, phenyl P, HEMA, DEPT, CQ, IADMAB and ethanol in the weight ratios shown in Table 8. The adhesive strength measurements and antimicrobial activity tests 1 and 2 were conducted in the manner described above. The results are shown in Table 8.

COMPARATIVE EXAMPLES 42–46

Adhesive compositions were prepared by blending MDPB, MDP, HEMA, BSS and DEPT in the weight ratios shown in Table 9. The adhesive strength measurements and antimicrobial activity tests 1 and 2 were conducted in the manner described above. The results are shown in Table 9.

As Table 1 clearly indicates, the adhesive compositions according to Example 1 through 4 all exhibited significantly high adhesive strength of about 20 MPa when applied on both the bovine dentin and enamel. In the antimicrobial activity test 1, they were confirmed to exhibit a very high antimicrobial activity, completely destroying the microorganisms adhered on the disk bottom during the primer treatment. A very high antimicrobial activity was confirmed in the test 2 as the microorganisms adhered on the cured surface were totally destroyed. On the other hand, as is clear from Table 5, Comparative Example 1 showed no antimicrobial activity either during the primer treatment or on the cured surface despite its favorable adhesive strength. Although antimicrobial activity was observed in Comparative Example 2, its adhesive strength is clearly lower compared to Examples 1 through 4. In Comparative Examples 5 and 6 wherein no polymerizable monomer having acidic group was blended, the adhesive strength is apparently lower than that of Examples 1 through 4, and their antimicrobial activity was not high enough to destroy the microorganisms during the primer treatment or on the cured surface. Comparative Examples 7 through 10 wherein no distilled water was blended and Comparative Examples 11 through 14 wherein HEMA was not blended showed an extremely high antimicrobial activity but the adhesive strength and the antimicrobial potence during the primer treatment were apparently lower than those of Examples 1 through 4. As for Comparative Examples 37 through 40 wherein distilled water was blended in an amount of 15 wt % which is less than the amount claimed in claim 1, the antimicrobial activity during the primer treatment was obviously lower than that of Examples 1 through 4, failing to destroy the microorganisms adhered on the disk bottom, although their adhesive strength was sufficiently high. Conversely, Comparative Example 41 wherein 80 wt % of distilled water was blended in excess of the amount claimed in claim 1 showed a significantly lower adhesive strength than Examples 1 through 4.

As is clear from Table 1, replacing the polymeric monomer having acidic group (phenyl P) used in Examples 1 through 4 with MDP (Examples 9 through 12) resulted in an extremely high adhesive strength of about 18 MPa both on the bovine dentin and enamel. They also exhibited a high antimicrobial activity during the primer treatment, totally destroying the microorganisms adhered on the disk bottom surface. In the antimicrobial activity test 2, similarly high activity of totally destroying the microorganisms adhered on the cured surface was confirmed. Conversely, as Table 6 clearly indicates, no antimicrobial activity was confirmed either during the primer treatment or on the cured surface for Comparative Example 15 despite its highly favorable adhesive strength. Although antimicrobial activity was observed in Comparative Example 16, its adhesive strength was apparently lower than that of Examples 9 through 12. With Comparative Examples 17 and 18 wherein no polymeric monomer having acidic group was blended, the adhesive strength was clearly lower than that of Examples 9 through 12 and their antimicrobial activity during the primer treatment or on the cured surface was not sufficient enough to totally destroy the microorganisms adhered. Although the antimicrobial activity was extremely high in Comparative Examples 9 through 22 wherein no distilled water was blended and Comparative Examples 23 through 26 wherein no HEMA was blended, the adhesive strength and antimicrobial activity during the primer treatment were apparently lower than those of Examples 9 through 12.

As is clear from Table 1, replacing the polymeric monomer having acidic groups (phenyl P) used in Examples 1 through 4 with methacrylic acid (Examples 13–16) also resulted in adhesive compositions with an extremely high adhesive strength of about 18 MPa both on the bovine dentin and enamel. Moreover, the antimicrobial activity test 1 confirmed a high activity of totally destroying the microorganisms adhered an the disk bottom surface during the primer treatment, while the antimicrobial activity test 2 confirmed a high activity of totally destroying the microorganisms adhered on the cured surface.

As is clearly shown in Table 2, replacing the polymeric monomer having acidic group used in Examples 1 through 4 (phenyl P) with 4-MET (Examples 17–20) resulted in a high adhesive strength of about 12 MPa on the bovine dentin and of about 15 MPa on the bovine enamel. Moreover, a high antimicrobial activity capable of totally destroying the microorganisms on the disk bottom surface during the primer treatment was confirmed in the test 1 and a similarly high activity capable of destroying the microorganisms on the cured surface in the test 2.

As is clearly shown in Table 2, replacing the polymeric monomer having acidic groups used in Examples 1 through 4 (phenyl P) with 4-META (Examples 21–24) resulted in a high adhesive strength of about 12 MPa on the bovine dentin and of about 15 MPa on the bovine enamel. Moreover, a high antimicrobial activity capable of totally destroying the microorganisms on the disk bottom surface during primer treatment was confirmed in the test 1 and a similarly high activity capable of destroying the microorganisms on the cured surface in the test 2.

As is also clear from Table 2, replacing the polymerizable monomer having acidic groups (phenyl P) used in Examples 1 through 4 with 4-AET (Examples 25–28) resulted in a high adhesive strength of about 12 MPa on the bovine dentin and of about 15 MPa on the bovine enamel. Moreover, a high antimicrobial activity capable of totally destroying the microorganisms on the disk bottom surface during the primer treatment was confirmed in the test 1 and a similarly high activity in the test 2 capable of totally destroying the microorganisms on the cured surface.

As is clearly shown in Table 3, the adhesive compositions of Examples 5 through 8 exhibited a high adhesive strength of about 6–7 MPa an the bovine dentin and of about 11–15 MPa on the bovine enamel. A high antimicrobial activity capable of totally destroying the microorganisms on the disk bottom surface during the primer treatment was confirmed in the test 1, while a similarly high activity was confirmed in the test 2 totally destroying the microorganisms on the cured surface. As is clear from Table 7, on the other hand, Comparative Example 3 failed to exhibit any antimicrobial activity either during the primer treatment or on the cured surface, although its adhesive strength was sufficiently high. While Comparative Example 4 exhibits antimicrobial activity, its adhesive strength is apparently lower than that of Examples 5 through 8. As for Comparative Examples 27 and 28 wherein no polymerizable monomer having acidic groups was blended, their adhesive strength is clearly lower than that of Examples 5 through 8; nor was their antimicrobial activity sufficient either during the primer treatment or on the cured surface. With Comparative Examples 29 through 32 wherein no distilled water was blended and Comparative Examples 33 through 36 wherein no HEMA was blended, the adhesive strength and the antimicrobial activity during the primer treatment were apparently lower than those of Examples 5 through 9, although their antimicrobial activity on the cured surface was extremely high. As for Comparative Examples 42 through 45 wherein distilled water was blended in an amount of 15 wt % which is less than the amount claimed in claim 1, the antimicrobial activity during the primer treatment was apparently lower than that of Examples 5 through 9, failing to destroy the microorganisms on the disk bottom surface, although their adhesive strength was sufficiently high. On the other hand, Comparative Example 46 wherein 80 wt % of distilled water was blended in excess of the amount claimed in claim 1 obviously had a lower adhesive strength when compared with that of Examples 5 through 9.

The present invention provides an antimicrobial adhesive composition for dental uses. According to the present invention, the antimicrobial adhesive composition is capable of preventing microbial invasion as the adhesion between the tooth and the restorative material is improved, of destroying the microorganisms remaining in the dental microstructure at the interface such as dentinal tubules and of destroying microorganisms which may invade the interface after the restorative material has been applied and adhered, to thereby prevent occurrence of secondary caries or infection of the dental pulps.

TABLE 1

Adhesive Composition, Adhesive Strength and Antimicrobial Property Test Results (Examples 1–4, 9–16)

| Component | Blend ratio (weight %) | | | | | | | | | | | |
| --- | --- | --- | --- | --- | --- | --- | --- | --- | --- | --- | --- | --- |
| | Example 1 | Example 2 | Example 3 | Example 4 | Example 9 | Example 10 | Example 11 | Example 12 | Example 13 | Example 14 | Example 15 | Example 16 |
| Phenyl P | 14.8 | 14.2 | 13.4 | 11.9 | — | — | — | — | — | — | — | — |
| MDP | — | — | — | — | 14.8 | 14.2 | 13.4 | 11.9 | — | — | — | — |
| Methacrylic acid | — | — | — | — | — | — | — | — | 14.8 | 14.2 | 13.4 | 11.9 |
| HEMA | 19.8 | 18.9 | 17.9 | 15.8 | 19.8 | 18.9 | 17.9 | 15.8 | 19.8 | 18.9 | 17.9 | 15.8 |
| Distilled water | 29.7 | 28.4 | 26.9 | 25.2 | 29.7 | 28.4 | 26.9 | 25.2 | 29.7 | 28.4 | 26.9 | 25.2 |
| Ethanol | 30.7 | 29.5 | 27.8 | 23.1 | 30.7 | 29.5 | 27.8 | 23.1 | 30.7 | 29.5 | 27.8 | 23.1 |
| DEPT | 2.0 | 2.0 | 2.0 | 2.0 | 2.0 | 2.0 | 2.0 | 2.0 | 2.0 | 2.0 | 2.0 | 2.0 |
| CQ | 1.0 | 1.0 | 1.0 | 1.0 | 1.0 | 1.0 | 1.0 | 1.0 | 1.0 | 1.0 | 1.0 | 1.0 |
| IADMAB | 1.0 | 1.0 | 1.0 | 1.0 | 1.0 | 1.0 | 1.0 | 1.0 | 1.0 | 1.0 | 1.0 | 1.0 |
| MDPB | 1.0 | 5.0 | 10.0 | 20.0 | 1.0 | 5.0 | 10.0 | 20.0 | 1.0 | 5.0 | 10.0 | 20.0 |
| Adhesive strength (Dentin) | 21.3 | 18.5 | 17.2 | 17.8 | 18.1 | 17.8 | 16.9 | 16.8 | 17.8 | 17.4 | 16.8 | 16.5 |
| Adhesive strength (Enamel) | 22.0 | 19.1 | 18.6 | 19.4 | 17.9 | 17.6 | 16.7 | 16.4 | 17.1 | 17.8 | 16.7 | 17.1 |
| (Antimicrobial property 1) bacterial proliferation on the disk bottom | — | — | — | — | — | — | — | — | — | — | — | — |
| (Antimicrobial property 2) death rate of bacteria on the surface | 100 | 100 | 100 | 100 | 100 | 100 | 100 | 100 | 100 | 100 | 100 | 100 |

TABLE 2

Adhesive Composition, Adhesive Strength and Antimicrobial Property Test Results (Examples 17–28)

| Component | Blend ratio (weight %) | | | | | | | | | | | |
| --- | --- | --- | --- | --- | --- | --- | --- | --- | --- | --- | --- | --- |
| | Example 17 | Example 18 | Example 19 | Example 20 | Example 21 | Example 22 | Example 23 | Example 24 | Example 25 | Example 26 | Example 27 | Example 28 |
| 4-MET | 14.8 | 14.2 | 13.4 | 11.9 | — | — | — | — | — | — | — | — |
| 4-META | — | — | — | — | 14.8 | 14.2 | 13.4 | 11.9 | — | — | — | — |
| 4-AET | — | — | — | — | — | — | — | — | 14.8 | 14.2 | 13.4 | 11.9 |
| HEMA | 19.8 | 18.9 | 17.9 | 15.8 | 19.8 | 18.9 | 17.9 | 15.8 | 19.8 | 18.9 | 17.9 | 15.8 |
| Distilled water | 29.7 | 28.4 | 26.9 | 25.2 | 29.7 | 28.4 | 26.9 | 25.2 | 29.7 | 28.4 | 26.9 | 25.2 |

TABLE 2-continued

Adhesive Composition, Adhesive Strength and Antimicrobial Property Test Results (Examples 17–28)

| Component | Blend ratio (weight %) | | | | | | | | | | | |
|---|---|---|---|---|---|---|---|---|---|---|---|---|
| | Example 17 | Example 18 | Example 19 | Example 20 | Example 21 | Example 22 | Example 23 | Example 24 | Example 25 | Example 26 | Example 27 | Example 28 |
| Ethanol | 30.7 | 29.5 | 27.8 | 23.1 | 30.7 | 29.5 | 27.8 | 23.1 | 30.7 | 29.5 | 27.8 | 23.1 |
| DEPT | 2.0 | 2.0 | 2.0 | 2.0 | 2.0 | 2.0 | 2.0 | 2.0 | 2.0 | 2.0 | 2.0 | 2.0 |
| CQ | 1.0 | 1.0 | 1.0 | 1.0 | 1.0 | 1.0 | 1.0 | 1.0 | 1.0 | 1.0 | 1.0 | 1.0 |
| IADMAD | 1.0 | 1.0 | 1.0 | 1.0 | 1.0 | 1.0 | 1.0 | 1.0 | 1.0 | 1.0 | 1.0 | 1.0 |
| MDPB | 1.0 | 5.0 | 10.0 | 20.0 | 1.0 | 5.0 | 10.0 | 20.0 | 1.0 | 5.0 | 10.0 | 20.0 |
| Adhesive strength (Dentin) | 12.1 | 12.3 | 13.2 | 11.8 | 13.2 | 13.4 | 12.8 | 11.5 | 14.2 | 14.3 | 13.3 | 12.7 |
| Adhesive strength (Enamel) | 15.1 | 14.9 | 14.5 | 13.9 | 15.4 | 14.8 | 14.7 | 13.8 | 15.3 | 14.9 | 14.5 | 13.9 |
| (Antimicrobial property 1) bacterial proliferation on the disk bottom | — | — | — | — | — | — | — | — | — | — | — | — |
| (Antimicrobial property 2) death rate of bacteria on the surface | 100 | 100 | 100 | 100 | 100 | 100 | 100 | 100 | 100 | 100 | 100 | 100 |

TABLE 3

Adhesive Composition, Adhesive Strength and Antimicrobial Property Test Results (Examples 5–8, 29–36)

| Component | Blend ratio (weight %) | | | | | | | | | | | |
|---|---|---|---|---|---|---|---|---|---|---|---|---|
| | Example 5 | Example 6 | Example 7 | Example 8 | Example 29 | Example 30 | Example 31 | Example 32 | Example 33 | Example 34 | Example 35 | Example 36 |
| HDP | 15.0 | 14.3 | 13.5 | 12.0 | — | — | — | — | — | — | — | — |
| Phenyl P | — | — | — | — | 15.0 | 14.3 | 13.5 | 12.0 | — | — | — | — |
| Methacrylic acid | — | — | — | — | — | — | — | — | 15.0 | 14.3 | 13.5 | 12.0 |
| HEMA | 20.0 | 19.0 | 18.0 | 16.0 | 20.0 | 19.0 | 18.0 | 16.0 | 20.0 | 19.0 | 18.0 | 16.0 |
| Distilled water | 54.0 | 52.3 | 49.5 | 44.0 | 54.0 | 52.3 | 49.5 | 44.0 | 54.0 | 52.3 | 49.5 | 44.0 |
| BSS | 5.0 | 4.7 | 4.5 | 4.0 | 5.0 | 4.7 | 4.5 | 4.0 | 5.0 | 4.7 | 4.5 | 4.0 |
| DEPT | 5.0 | 4.7 | 4.5 | 4.0 | 5.0 | 4.7 | 4.5 | 4.0 | 5.0 | 4.7 | 4.5 | 4.0 |
| MDPB | 1.0 | 5.0 | 10.0 | 20.0 | 1.0 | 5.0 | 10.0 | 20.0 | 1.0 | 5.0 | 10.0 | 20.0 |
| Adhesive strength (Dentin) | 7.2 | 6.8 | 6.5 | 5.8 | 7.9 | 8.0 | 6.9 | 6.5 | 7.8 | 7.6 | 7.4 | 7.1 |
| Adhesive strength (Enamel) | 14.8 | 13.2 | 13.7 | 11.4 | 15.8 | 15.2 | 14.8 | 13.9 | 13.9 | 14.5 | 13.2 | 11.8 |
| (Antimicrobial property 1) bacterial proliferation on the disk bottom | — | — | — | — | — | — | — | — | — | — | — | — |
| (Antimicrobial property 2) death rate of bacteria on the surface | 100 | 100 | 100 | 100 | 100 | 100 | 100 | 100 | 100 | 100 | 100 | 100 |

TABLE 4

Adhesive Composition, Adhesive Strength and Antimicrobial Property Test Results (Examples 37–48)

| Component | Blend ratio (weight %) | | | | | | | | | | | |
|---|---|---|---|---|---|---|---|---|---|---|---|---|
| | Example 37 | Example 38 | Example 39 | Example 40 | Example 41 | Example 42 | Example 43 | Example 44 | Example 45 | Example 46 | Example 47 | Example 48 |
| Phenyl P | 15.0 | 14.3 | 13.5 | 12.0 | — | — | — | — | 15.0 | 14.3 | 13.5 | 12.0 |
| MDP | — | — | — | — | 15.0 | 14.3 | 13.5 | 12.0 | — | — | — | — |
| HEMA | 20.0 | 19.0 | 18.0 | 16.0 | 20.0 | 19.0 | 18.0 | 16.0 | 20.0 | 19.0 | 18.0 | 16.0 |
| Distilled water | 54.0 | 52.3 | 49.5 | 44.0 | 54.0 | 52.3 | 49.5 | 44.0 | 54.0 | 52.3 | 49.5 | 44.0 |
| BSS | 5.0 | 4.7 | 4.5 | 4.0 | 5.0 | 4.7 | 4.5 | 4.0 | 5.0 | 4.7 | 4.5 | 4.0 |
| DEPT | 5.0 | 4.7 | 4.5 | 4.0 | 5.0 | 4.7 | 4.5 | 4.0 | 5.0 | 4.7 | 4.5 | 4.0 |
| D-301 monomer | 1.0 | 5.0 | 10.0 | 20.0 | 1.0 | 5.0 | 10.0 | 20.0 | — | — | — | — |
| VB-16 monomer | — | — | — | — | — | — | — | — | 1.0 | 5.0 | 10.0 | 20.0 |
| Adhesive strength (Dentin) | 8.5 | 8.8 | 8.2 | 7.9 | 8.8 | 7.9 | 8.2 | 7.4 | 8.9 | 8.4 | 7.8 | 7.3 |
| Adhesive strength (Enamel) | 15.8 | 16.2 | 15.9 | 14.8 | 15.2 | 14.9 | 15.2 | 14.2 | 14.9 | 15.0 | 14.2 | 13.9 |
| (Antimicrobial property 1) bacterial proliferation on the disk bottom | — | — | — | — | — | — | — | — | — | — | — | — |
| (Antimicrobial property 2) death rate of bacteria on the surface | 100 | 100 | 100 | 100 | 100 | 100 | 100 | 100 | 100 | 100 | 100 | 100 |

TABLE 5

Adhesive Composition, Adhesive Strength and Antimicrobial Property Test Results (Comparative Examples 1–2, 5–14)

| Component | Blend ratio (weight %) | | | | | | | | | | | |
|---|---|---|---|---|---|---|---|---|---|---|---|---|
| | Comp. Example 1 | Comp. Example 2 | Comp. Example 5 | Comp. Example 6 | Comp. Example 7 | Comp. Example 8 | Comp. Example 9 | Comp. Example 10 | Comp. Example 11 | Comp. Example 12 | Comp. Example 13 | Comp. Example 14 |
| Phenyl P | 15.0 | 10.3 | 0.0 | 0.0 | 21.6 | 20.7 | 19.5 | 17.3 | 18.7 | 18.0 | 17.0 | 15.0 |
| HEMA | 20.0 | 13.8 | 23.5 | 18.8 | 28.9 | 27.6 | 26.1 | 23.0 | 0.0 | 0.0 | 0.0 | 0.0 |
| Distilled water | 30.0 | 20.6 | 35.2 | 28.1 | 0.0 | 0.0 | 0.0 | 0.0 | 37.5 | 35.9 | 33.9 | 30.0 |
| Ethanol | 31.0 | 21.3 | 36.3 | 29.1 | 44.5 | 42.7 | 40.4 | 35.7 | 38.8 | 37.1 | 35.1 | 31.0 |
| DEPT | 2.0 | 2.0 | 2.0 | 2.0 | 2.0 | 2.0 | 2.0 | 2.0 | 2.0 | 2.0 | 2.0 | 2.0 |
| CQ | 1.0 | 1.0 | 1.0 | 1.0 | 1.0 | 1.0 | 1.0 | 1.0 | 1.0 | 1.0 | 1.0 | 1.0 |
| IADMAB | 1.0 | 1.0 | 1.0 | 1.0 | 1.0 | 1.0 | 1.0 | 1.0 | 1.0 | 1.0 | 1.0 | 1.0 |
| MDPB | 0.0 | 30.0 | 1.0 | 20.0 | 1.0 | 5.0 | 10.0 | 20.0 | 1.0 | 5.0 | 10.0 | 20.0 |
| Adhesive strength (Dentin) | 19.5 | 6.1 | 2.8 | 4.2 | 3.3 | 2.7 | 3.1 | 4.1 | 1.2 | 1.3 | 1.9 | 1.3 |
| Adhesive strength (Enamel) | 19.5 | 8.1 | 3.2 | 4.6 | 2.9 | 2.7 | 3.2 | 2.1 | 1.6 | 1.8 | 1.7 | 1.4 |
| (Antimicrobial property 1) bacterial proliferation on the disk bottom | ++ | — | + | + | + | + | + | + | + | + | + | + |
| (Antimicrobial property 2) death rate of bacteria on the surface | 0 | 100 | 60 | 80 | 100 | 100 | 100 | 100 | 100 | 100 | 100 | 100 |

TABLE 6

Adhesive Composition, Adhesive Strength and Antimicrobial Property Test Results (Comparative Examples 15–26)

| Component | Comp. Example 15 | Comp. Example 16 | Comp. Example 17 | Comp. Example 18 | Comp. Example 19 | Comp. Example 20 | Comp. Example 21 | Comp. Example 22 | Comp. Example 23 | Comp. Example 24 | Comp. Example 25 | Comp. Example 26 |
|---|---|---|---|---|---|---|---|---|---|---|---|---|
| MDP | 15.0 | 10.3 | 0.0 | 0.0 | 21.6 | 20.7 | 19.5 | 17.3 | 18.7 | 18.0 | 17.0 | 15.0 |
| HEMA | 20.0 | 13.8 | 23.5 | 18.8 | 28.9 | 27.6 | 26.1 | 23.0 | 0.0 | 0.0 | 0.0 | 0.0 |
| Distilled water | 30.0 | 20.6 | 35.2 | 28.1 | 0.0 | 0.0 | 0.0 | 0.0 | 37.5 | 35.9 | 33.9 | 30.0 |
| Ethanol | 31.0 | 21.3 | 36.3 | 29.1 | 44.5 | 42.7 | 40.4 | 35.7 | 38.8 | 37.1 | 35.1 | 31.0 |
| DEPT | 2.0 | 2.0 | 2.0 | 2.0 | 2.0 | 2.0 | 2.0 | 2.0 | 2.0 | 2.0 | 2.0 | 2.0 |
| CQ | 1.0 | 1.0 | 1.0 | 1.0 | 1.0 | 1.0 | 1.0 | 1.0 | 1.0 | 1.0 | 1.0 | 1.0 |
| IADMAB | 1.0 | 1.0 | 1.0 | 1.0 | 1.0 | 1.0 | 1.0 | 1.0 | 1.0 | 1.0 | 1.0 | 1.0 |
| MDPB | 0.0 | 30.0 | 1.0 | 20.0 | 1.0 | 5.0 | 10.0 | 20.0 | 1.0 | 5.0 | 10.0 | 20.0 |
| Adhesive strength (Dentin) | 20.1 | 7.2 | 3.1 | 2.9 | 2.3 | 1.9 | 1.7 | 1.9 | 1.8 | 2.0 | 1.8 | 1.8 |
| Adhesive strength (Enamel) | 19.8 | 6.8 | 2.7 | 2.2 | 2.1 | 1.6 | 1.7 | 2.1 | 1.9 | 1.6 | 1.5 | 1.2 |
| (Antimicrobial property 1) bacterial proliferation on the disk bottom | ++ | − | + | + | + | + | + | + | + | + | + | + |
| (Antimicrobial property 2) death rate of bacteria on the surface | 0 | 100 | 20 | 90 | 100 | 100 | 100 | 100 | 100 | 100 | 100 | 100 |

TABLE 7

Adhesive Composition, Adhesive Strength and Antimicrobial Property Test Results (Comparative Examples 3–4, 27–36)

| Component | Comp. Example 3 | Comp. Example 4 | Comp. Example 27 | Comp. Example 28 | Comp. Example 29 | Comp. Example 30 | Comp. Example 31 | Comp. Example 32 | Comp. Example 33 | Comp. Example 34 | Comp. Example 35 | Comp. Example 36 |
|---|---|---|---|---|---|---|---|---|---|---|---|---|
| MDP | 15.0 | 10.5 | 0.0 | 0.0 | 38.1 | 36.9 | 35.1 | 31.3 | 19.1 | 18.4 | 17.6 | 15.6 |
| HEMA | 20.0 | 14.0 | 23.3 | 18.8 | 50.9 | 49.6 | 46.9 | 41.7 | 0.0 | 0.0 | 0.0 | 0.0 |
| Distilled water | 55.0 | 38.5 | 64.1 | 51.8 | 0.0 | 0.0 | 0.0 | 0.0 | 69.9 | 67.6 | 64.4 | 57.4 |
| BSS | 5.0 | 3.5 | 5.8 | 4.7 | 5.0 | 4.5 | 4.0 | 3.5 | 5.0 | 4.5 | 4.0 | 3.5 |
| DEPT | 5.0 | 3.5 | 5.8 | 4.7 | 5.0 | 4.5 | 4.0 | 3.5 | 5.0 | 4.5 | 4.0 | 3.5 |
| MDPB | 0.0 | 30.0 | 1.0 | 20.0 | 1.0 | 5.0 | 10.0 | 20.0 | 1.0 | 5.0 | 10.0 | 20.0 |
| Adhesive strength (Dentin) | 6.2 | 3.1 | 0.8 | 1.2 | 1.2 | 0.9 | 0.8 | 0.8 | 0.9 | 0.8 | 0.5 | 0.6 |
| Adhesive strength (Enamel) | 13.9 | 7.8 | 1.2 | 1.5 | 1.8 | 1.3 | 1.1 | 1.0 | 1.3 | 1.4 | 0.9 | 0.7 |
| (Antimicrobial property 1) bacterial proliferation on the disk bottom | + | − | + | + | + | + | + | + | + | + | + | + |
| (Antimicrobial property 2) death rate of bacteria on the surface | 0 | 100 | 20 | 90 | 100 | 100 | 100 | 100 | 100 | 100 | 100 | 100 |

TABLE 8

Adhesive Composition, Adhesive Strength and Antimicrobial Property Test Results (Comparative Examples 37–41)

| Component | Comp. Example 37 | Comp. Example 38 | Comp. Example 39 | Comp. Example 40 | Comp. Example 41 |
|---|---|---|---|---|---|
| | Blend Ratio (wt %) | | | | |
| Phenyl P | 18.2 | 17.5 | 16.2 | 13.9 | 5.0 |
| HEMA | 24.3 | 23.4 | 22.6 | 18.5 | 10.0 |
| Distilled water | 15.0 | 15.0 | 15.0 | 15.0 | 80.0 |
| Ethanol | 37.5 | 36.1 | 33.2 | 28.6 | 0.0 |
| DEPT | 2.0 | 2.0 | 2.0 | 2.0 | 2.0 |
| CQ | 1.0 | 1.0 | 1.0 | 1.0 | 1.0 |
| IADMAB | 1.0 | 1.0 | 1.0 | 1.0 | 1.0 |
| MDPB | 1.0 | 5.0 | 10.0 | 20.0 | 1.0 |
| Adhesive strength (Dentin) | 15.3 | 14.9 | 14.8 | 14.1 | 0.3 |
| Adhesive strength (Enamel) | 16.2 | 15.9 | 15.2 | 15.4 | 1.1 |
| (Antimicrobial property 1) bacterial proliferation on the disk bottom | + | + | + | + | − |
| (Antimicrobial property 2) death rate of bacteria on the surface | 100 | 100 | 100 | 100 | 100 |

TABLE 9

Adhesive Composition, Adhesive Strength and Antimicrobial Property Test Results (Comparative Examples 42–46)

| Component | Comp. Example 42 | Comp. Example 43 | Comp. Example 44 | Comp. Example 45 | Comp. Example 46 |
|---|---|---|---|---|---|
| | Blend Ratio (wt %) | | | | |
| MDP | 31.7 | 30.5 | 28.7 | 24.9 | 5.0 |
| HEMA | 42.3 | 40.5 | 38.3 | 33.1 | 10.0 |
| Distilled water | 15.0 | 15.0 | 15.0 | 15.0 | 80.0 |
| BSS | 5.0 | 4.5 | 4.0 | 3.5 | 2.0 |
| DEPT | 5.0 | 4.5 | 4.0 | 3.5 | 2.0 |
| MDPB | 1.0 | 5.0 | 10.0 | 20.0 | 1.0 |
| Adhesive strength (Dentin) | 6.3 | 5.9 | 6.8 | 5.9 | 0.5 |
| Adhesive strength (Enamel) | 12.2 | 11.9 | 13.2 | 12.4 | 0.9 |
| (Antimicrobial property 1) bacterial proliferation on the disk bottom | + | + | + | + | − |
| (Antimicrobial property 2) death rate of bacteria on the surface | 100 | 100 | 100 | 100 | 100 |

What is claimed as new and is desired to be secured by Letters Patent of the United States is:

1. A monomeric, polymerizable, antimicrobial, adhesive composition for dental use, said composition comprising a blend of ingredients comprising:

(A) 0.01 to 25% by weight (wt %) of an antimicrobial ethylenically unsaturated polymerizable monomer, (B) 5 to 40 wt % of an ethylenically unsaturated (meth) acryloyl or vinyl polymerizable monomer having at least one acidic group, (C) 10 to 50 wt % of an ethylenically unsaturated (meth) acryloyl or vinyl polymerizable monomer having at least one alcoholic hydroxy group, (D) 20 to 75 wt % of water, and (E) a polymerization catalyst capable of ethylenically polymerizing said monomers.

2. The antimicrobial adhesive composition for dental use as claimed in claim 1 wherein said antimicrobial polymerizable monomer is represented by the following Chemical Formula 1:

Chemical Formula 1

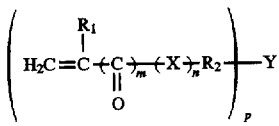

$R_1$=H, $CH_3$ $R_2$=Alkylene group of $C_8$–$C_{25}$

X=O,S,

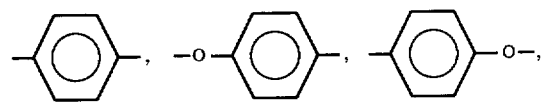

—$CH_2O$—, —$OCH_2$— m=0 or 1 n=0 or 1 p=1–3

Y=

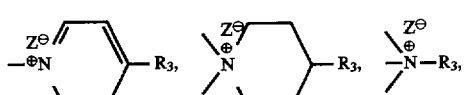

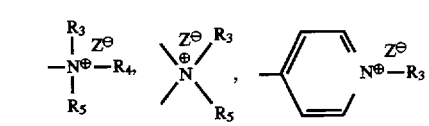

$R_3$, $R_4$, $R_5$=–(X)$_q$–$R_6$–W

X=O,S,

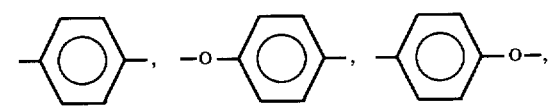

—$CH_2O$—, —$OCH_2$—

$R_6$=Alkylene group of $C_8$–$C_{25}$

W=–H, —$CH_3$,

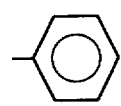

q=0 or 1

Z=Cl, Br, I.

3. The antimicrobial adhesive composition for dental use as claimed in claim 1 wherein said antimicrobial polymerizable monomer is represented by the following Chemical Formula 2:

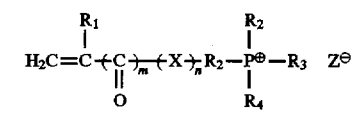

Chemical Formula 2

$R_1 = CH_3, H$
$X = O, S,$

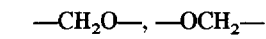

$-CH_2O-, -OCH_2-$
m=0 or 1
n=0 or 1
$R_2, R_3, R_4 = -(X)_q - R_5 - W$
$R_5 =$ Alkylene group of $C_8-C_{25}$
$W = -H, CH_3,$

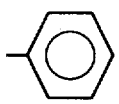

q=0 or 1
Z=Cl, Br, I.

4. The antimicrobial adhesive composition for dental use as claimed in claim 1 wherein said antimicrobial polymerizable monomer is represented by the following Chemical Formula 3:

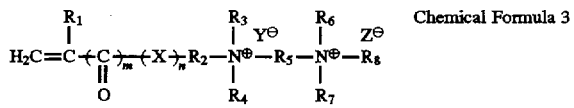

Chemical Formula 3

$R_1 = H, CH_3$
$R_2 =$ Alkylene group of $C_8-C_{25}$
$X = O, S,$

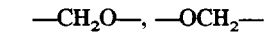

$-CH_2O-, -OCH_2-$
m=0 or 1
n=0 or 1
$R_3, R_4, R_6, R_7 = H$ or $C_1-C_{20}$ alkyl
$R_5 =$ Alkylene group of $C_1-C_{20}$
$R_8 = H,$ or $C_1-C_{20}$ alkyl, or

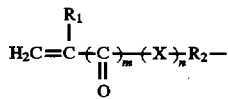

Z, Y=Cl, Br, I.

5. The antimicrobial adhesive composition for dental use as claimed in claim 1 wherein said antimicrobial polymerizable monomer is represented by the following Chemical Formula 4:

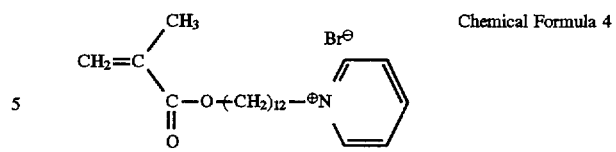

Chemical Formula 4

6. The antimicrobial adhesive composition for dental use as claimed in claim 1, comprising 0.1–20 wt. % of said antimicrobial polymerizable monomer.

7. The antimicrobial adhesive composition for dental use as claimed in claim 1, comprising 10–30 wt. % of said polymerizable monomer having at least one acidic group.

8. The antimicrobial adhesive composition for dental use as claimed in claim 1, comprising 15–40 wt. % of said polymerizable monomer having at least one alcoholic hydroxy group.

9. The antimicrobial adhesive composition for dental use as claimed in claim 1, comprising 25–60 wt. % water.

10. The antimicrobial adhesive composition for dental use as claimed in claim 1, comprising 2–15 wt. % of said polymerization catalyst.

11. The antimicrobial adhesive composition for dental use as claimed in claim 1, wherein said polymerizable monomer having at least one acidic group is selected from the group consisting of 2-(meth)acryloylethoxyethyl dihydrogen phosphate, 6-(meth)acryloyloxyhexyl dihydrogen phosphate, 10-(meth)acryloyloxydecyl dihydrogen phosphate, 2-(meth)acryloyloxyethylphenyl dihydrogen phosphate, bis(2-(meth)acryloyloxyethyl) hydrogen phosphate, 2-(meth)acryloyloxyethyl hydrogen phenylphosphate, 2-(meth)acryloyloxyethyl hydrogen anicylphosphate, 6-(meth)acryloyloxyhexyl phosphinate, N-(10-phosphonodecyl)(meth)acrylamide, 4-vinylbenzene phosphate, (meth)acrylic acid, succinic acid mono(2-(meth)-acryloyloxyethyl), isophthalic acid (2-(meth)acryloyloxyethyl), 4-(meth)acryloylethyl trimellitic acid, 11,11-dicarboxylundecyl (meth)acrylate, N-(meth)acryloylalamine, N-(meth)acryloyl-5-aminosalicylic acid, 4-vinylbenzoic acid, 2-(meth)acrylamide-2-methylpropane sulfonic acid, styrene sulfonic acid, anhydrides thereof and mixtures thereof.

12. The antimicrobial adhesive composition for dental use as claimed in claim 1, wherein said polymerizable monomer having at least one alcoholic hydroxy group is selected from the group consisting of 2-hydroxyethyl(meth)acrylate, propylene-glycolmono(meth)acrylate, glycerine mono(meth)acrylate, erythritol mono(meth)acrylate, pentaerythritol-di(meth)acrylate, 1,2-bis(3-methacryloyloxy-2-hydroxypropoxy)ethane, N-methylol (meth)acrylamide, N-hydroxyethyl(meth)acrylamide, N,N (dihydroxyethyl)(meth)acrylamide and mixtures thereof.

13. A cured polymerizable composition, obtained by polymerizing the composition of claim 1.

14. A monomeric, polymerizable, antimicrobial, adhesive composition for dental use, said composition comprising a blend of ingredients comprising:

(A) 0.01 to 25% by weight (wt %) of an antimicrobial ethylenically unsaturated polymerizable monomer, (B) 5 to 40 wt % of an ethylenically unsaturated (meth) acryloyl or vinyl polymerizable monomer having at least one acidic group, (C) 10 to 50 wt % of an ethylenically unsaturated (meth) acryloyl or vinyl polymerizable monomer having at least one alcoholic hydroxy group, said hydroxyl group containing monomer being selected from group consisting of 2-hydroxyethyl(meth)acrylate, propyleneglycolmono(meth)acrylate, glycerinemono(meth)acrylate, erythritolmono(meth)acrylate, penthaerythritol-di(meth)acrylate, 1,2-bis(3-methacroyloyloxy-2-hydroxypropoxy)ethane, N-methylol(meth)acrylamide, N-hydroxyethyl(meth)acrylamide, and N,N(dihydroxy-ethyl)(meth)acrylamide, (D) 20 to 75 wt % of water, and (E) a polymerization catalyst capable of ethylenically polymerizing said monomers.

* * * * *